(12) United States Patent
Shaw et al.

(10) Patent No.: US 8,496,600 B2
(45) Date of Patent: Jul. 30, 2013

(54) NON-REUSABLE COLLECTION DEVICE FOR BODILY FLUIDS

(75) Inventors: Thomas J. Shaw, Frisco, TX (US); Mark Small, Leonard, TX (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 304 days.

(21) Appl. No.: 12/846,402

(22) Filed: Jul. 29, 2010

(65) Prior Publication Data

US 2010/0317999 A1 Dec. 16, 2010

Related U.S. Application Data

(63) Continuation-in-part of application No. 12/136,462, filed on Jun. 10, 2008, now abandoned.

(51) Int. Cl.
*A61B 5/00* (2006.01)

(52) U.S. Cl.
USPC .......................................... 600/576; 604/110

(58) Field of Classification Search
USPC .......................................... 600/576; 604/110
See application file for complete search history.

(56) References Cited

U.S. PATENT DOCUMENTS

| | | | |
|---|---|---|---|
| 4,813,426 A * | 3/1989 | Haber et al. | ................... 600/576 |
| 5,423,758 A | 6/1995 | Shaw | |
| 5,685,863 A | 11/1997 | Botich et al. | |
| 5,779,679 A | 7/1998 | Shaw | |
| 5,957,887 A | 9/1999 | Osterlind et al. | |
| 6,210,371 B1 | 4/2001 | Shaw | |
| 2002/0068907 A1 | 6/2002 | Dysarz | |
| 2003/0078540 A1 | 4/2003 | Saulenas et al. | |
| 2004/0019329 A1 | 1/2004 | Erskine | |
| 2005/0288607 A1 | 12/2005 | Konrad | |
| 2006/0155244 A1 | 7/2006 | Popov | |
| 2006/0235354 A1 | 10/2006 | Kaal et al. | |
| 2009/0306601 A1 | 12/2009 | Shaw et al. | |

\* cited by examiner

*Primary Examiner* — Max Hindenburg
*Assistant Examiner* — Renee Danega
(74) *Attorney, Agent, or Firm* — Ross Barnes LLP; Monty L. Ross; Robin L. Barnes

(57) ABSTRACT

A non-reusable device for collecting bodily fluids such as vascular blood from a patient, the device being configured for example to receive a blood collection tube and having a retractable needle attached to a rearwardly biased needle holder that is constrained prior to needle retraction by a rotatably mounted lug ring and that is released during retraction by depressing a trigger pivotably connected to the body of the device to rotate the lug ring, whereby the needle holder is driven into a retraction cavity disposed inside the trigger and the front tip of the needle is retained inside the body of the device.

21 Claims, 6 Drawing Sheets

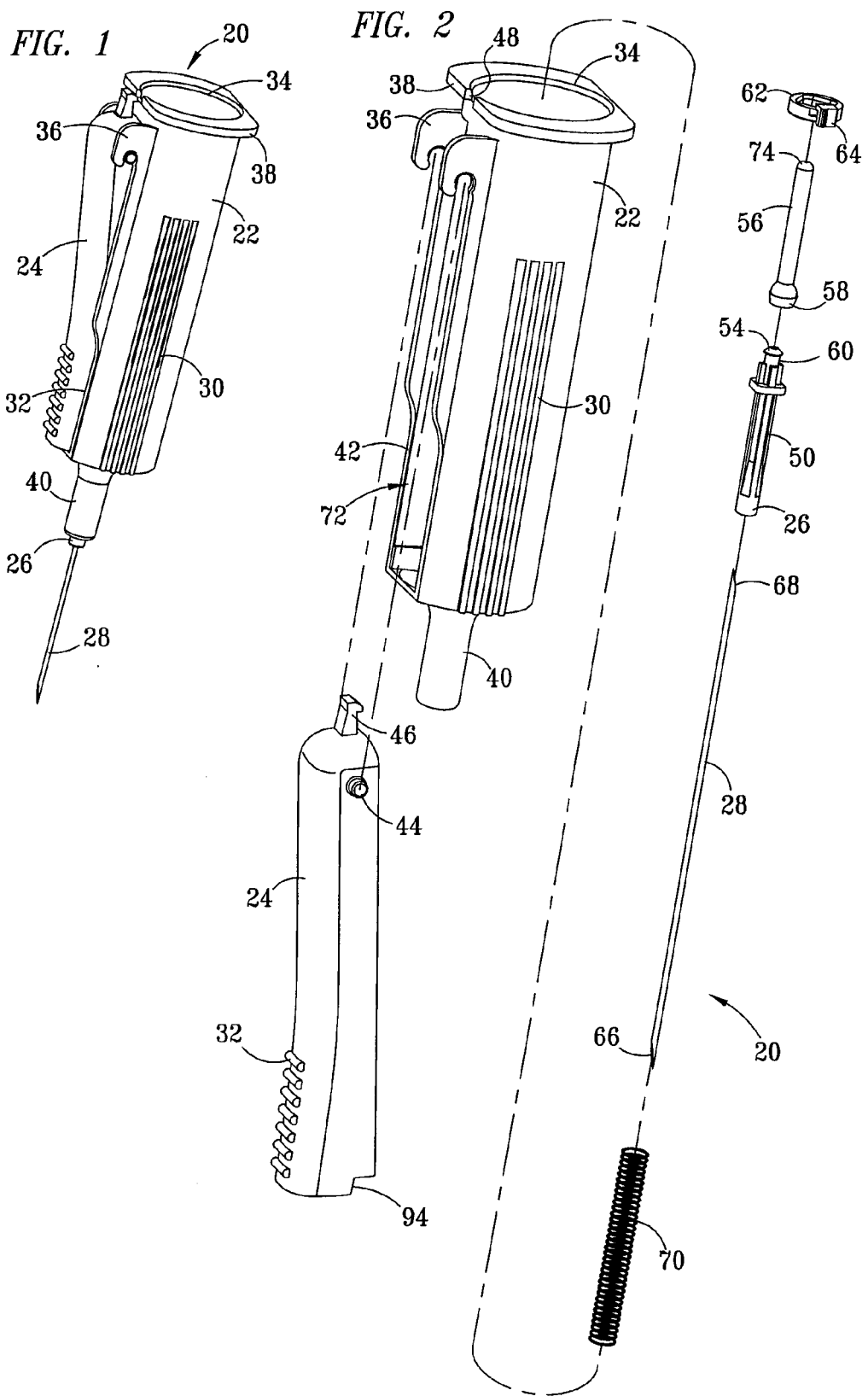

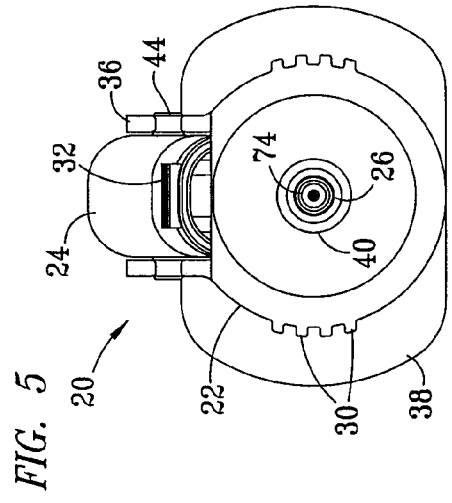
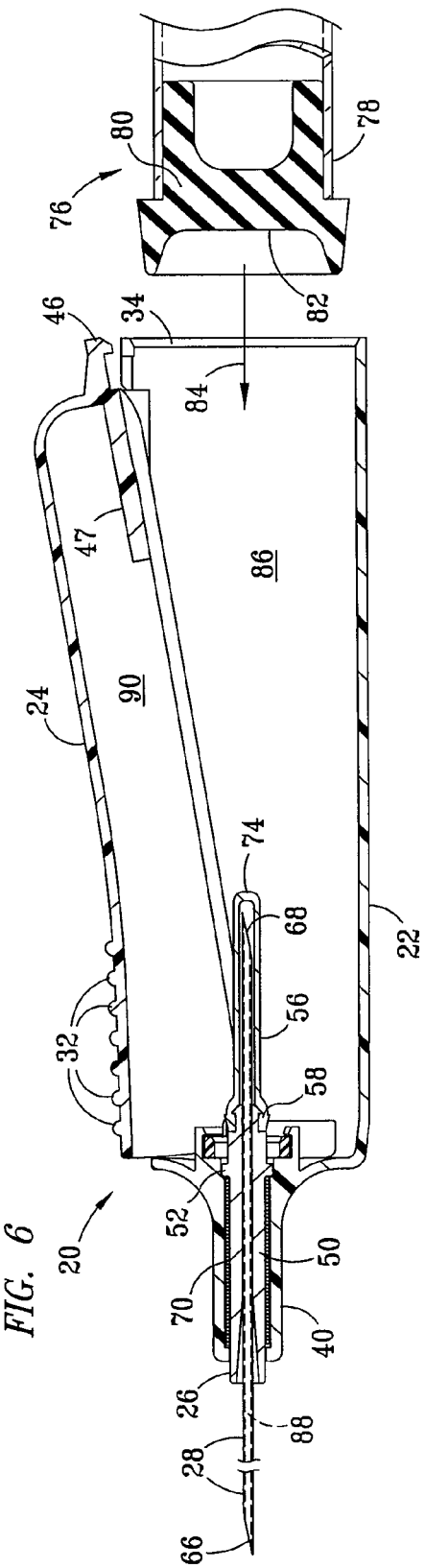

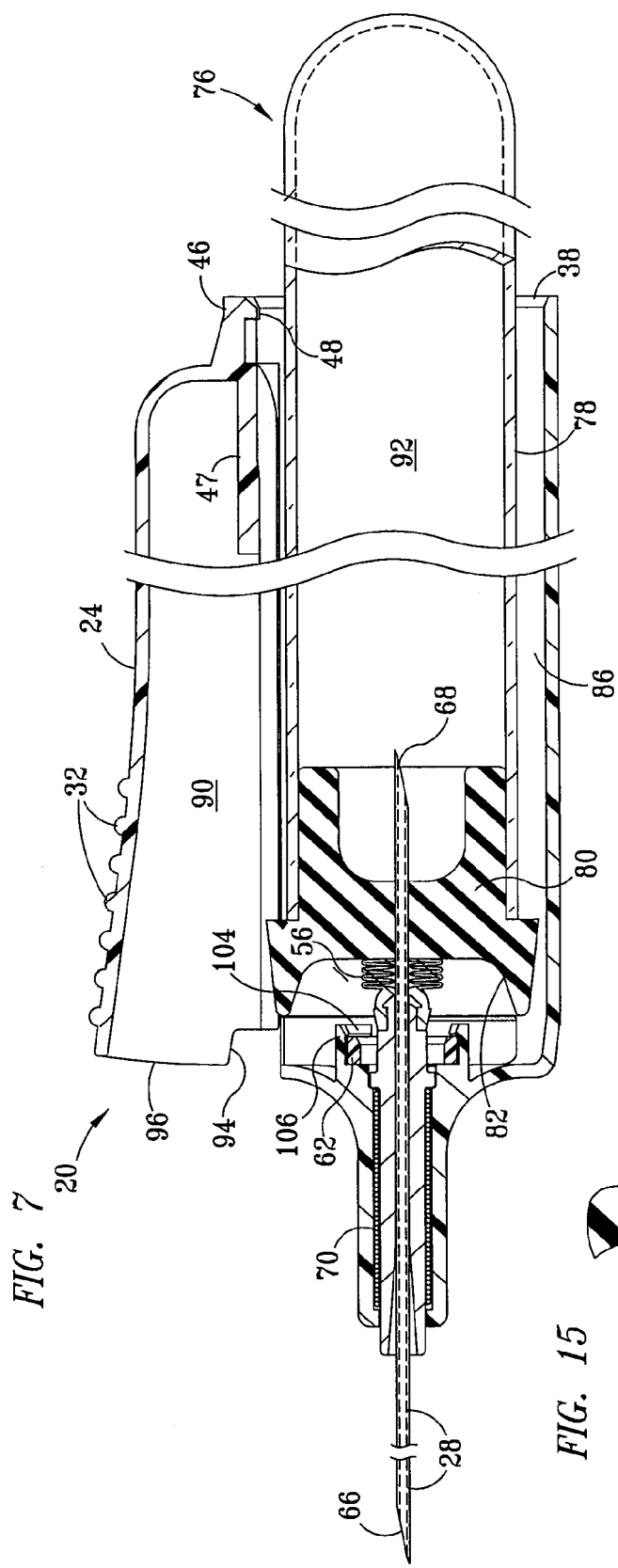
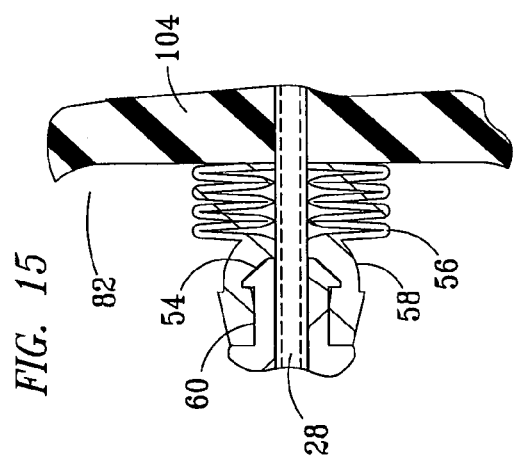

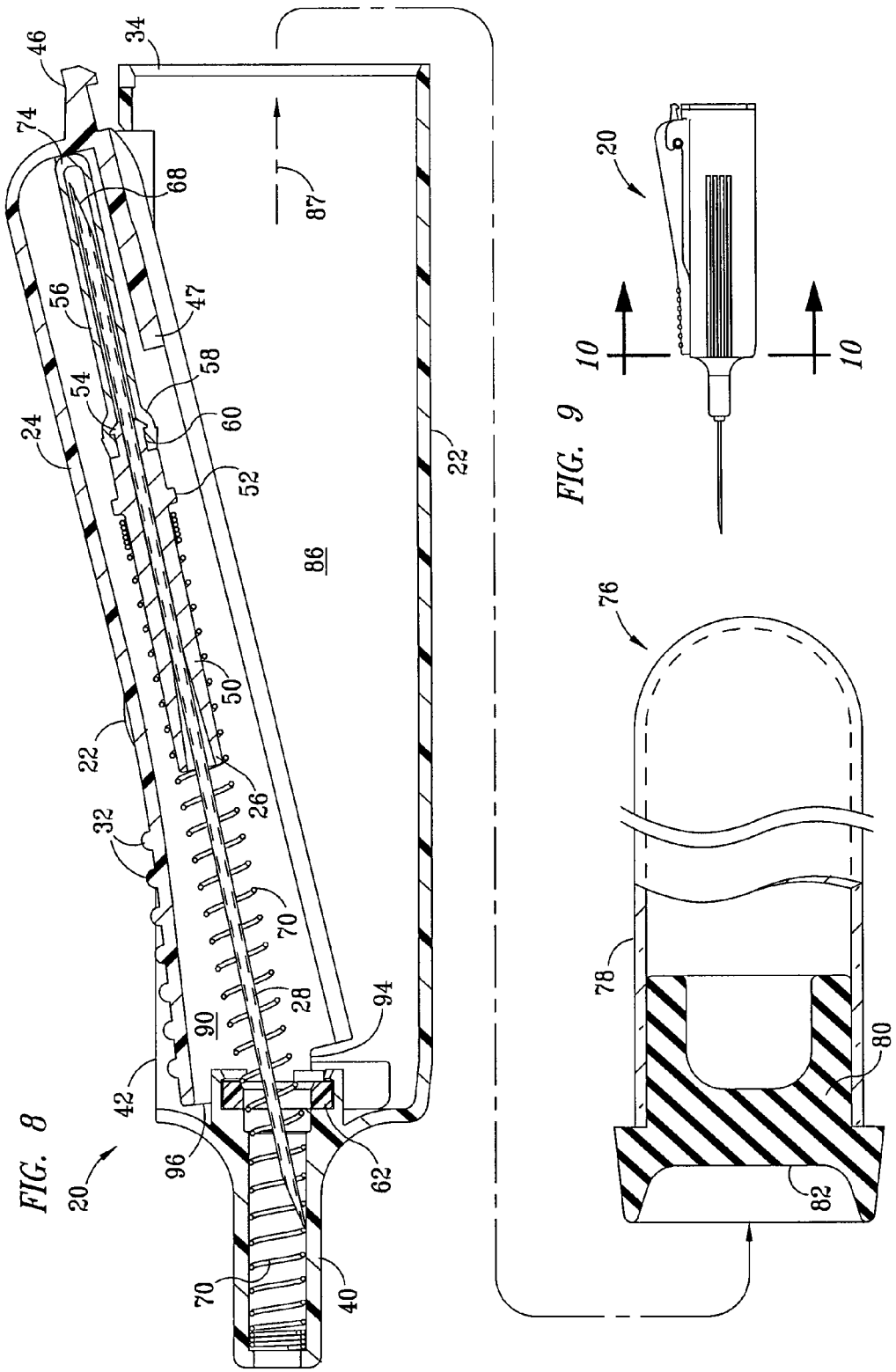

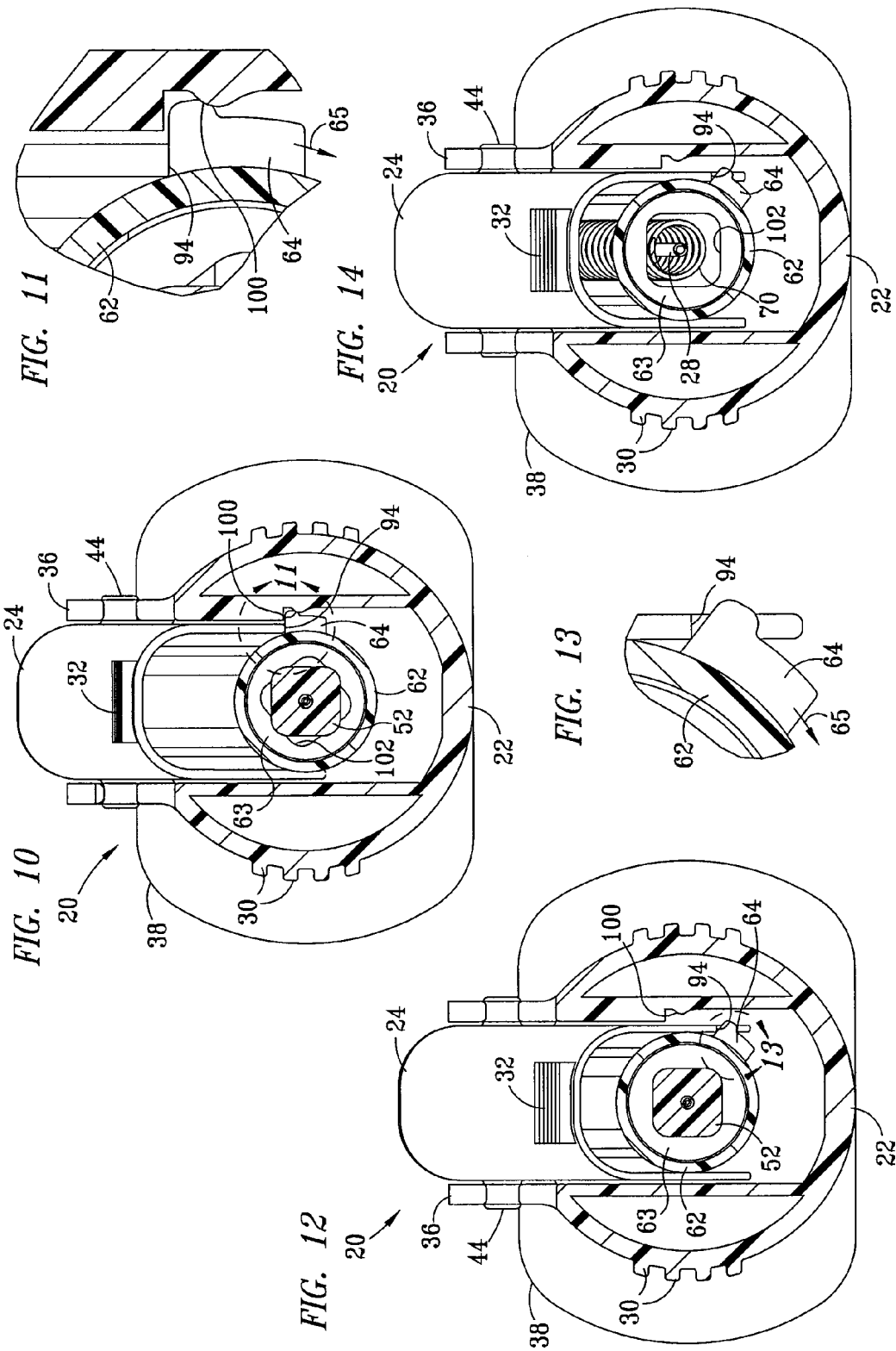

NON-REUSABLE COLLECTION DEVICE FOR BODILY FLUIDS

CROSS-REFERENCE TO RELATED APPLICATION

This application is a continuation-in-part of U.S. patent application Ser. No. 12/136,462, filed Jun. 10, 2008 now abandoned.

BACKGROUND OF THE INVENTION

1. Field of the Invention

This invention relates to a medical device that is useful for collecting bodily fluids from a patient, and more particularly for example, to a vascular blood collection device that is non-reusable and that provides protection against accidental needle sticks.

2. Description of Related Art

Conventional devices used to draw vascular blood or other bodily fluids from a patient leave the needle tip exposed when it is withdrawn from the patient, thereby subjecting users of the devices to possible needle sticks and to contamination by contact with pathogens that are present in the fluid. A device is needed that provides greater protection to both the user and the patient, that is not susceptible to reuse with other patients, that is convenient to use, that can be used, for example, with conventional blood collection tubes, and that can be reliably manufactured in high volumes at relatively low cost. Such a device is disclosed in this application.

SUMMARY OF THE INVENTION

The invention disclosed herein is a medical device that can be used to draw blood or other bodily fluids from a patient or animal using conventional collection tubes having an elastomeric, typically rubber, stopper at one end. The forwardly extending end of the device desirably has a sharp needle tip that is insertable, for example, into a patient's vein. The rear end of the needle desirably also has a sharp needle tip that can be inserted through the elastomeric closure, usually a rubber stopper, that seals the open end of a blood collection tube. The rear end of the needle is initially covered with a flexible elastomeric sheath that can be penetrated by the rearwardly extending needle tip and then pushed forwardly and collapsed as the needle tip also penetrates the closure to establish fluid communication through the needle between the patient's vein and the interior of the blood collection tube. The collapsible elastomeric sheath over the rearwardly facing needle tip also prevents fluid from escaping out the rear of the needle prior to the time that the needle is inserted into the blood collection tube. Once the desired fluid volume has been collected, and as the collection tube is withdrawn out of contact with the needle tip, the collapsed elastomeric sheath expands simultaneously to its original position covering the needle tip. This prevents any blood remaining in the needle from exiting the needle or the rear of the device prior to retraction.

Another desirable feature of the present invention is that the forwardly extending needle tip can be retracted inside the body of the device to prevent accidental needle sticks. This retraction is desirably initiated without first removing the needle from the patient's body by depressing a trigger that is hinged near the rear of the device. When the forward end of the trigger is depressed relative to the body of the device, the rearwardly extending needle tip is propelled by a compressed retraction spring into a retraction cavity inside the trigger. After the retraction spring expands during needle retraction, the front needle tip remains inside the body of the device Another desirable feature of the present invention is the release mechanism that is used to initiate needle retraction. Prior to retraction, the needle is affixed to a needle holder that is biased rearwardly by a compressed retraction spring and is retained in that position by a lug ring rotatably mounted inside the body of the device. As the trigger is depressed to initiate needle retraction following collection of a bodily fluid, the trigger contacts a lug that projects radially from the lug ring, causing the lug ring to rotate inside the body of the device. As the lug ring rotates, an aperture in the ring is moved into alignment with a cooperatively shaped transverse flange on the needle holder, thereby allowing the previously constrained needle holder to pass through the aperture. As the transverse flange passes through the aperture in the lug ring, the compressed retraction spring is released to drive the needle holder rearwardly into a retraction cavity inside the trigger. This rotating release mechanism is believed to be unlike that used to release a retraction spring in any prior art device having a retractable needle, and combines a reliable hold with a smoothly operating release action requiring the application of a relatively low triggering force by a clinician using the device.

According to a preferred embodiment of the invention, a non-reusable device is disclosed for collecting bodily fluids such as vascular blood from a patient, the device being configured for example to receive a blood collection tube and having a retractable needle attached to a rearwardly biased needle holder that is constrained prior to needle retraction by a rotatably mounted lug ring and that is released during retraction by depressing a trigger pivotably connected to the body of the device to rotate the lug ring, whereby the needle holder is driven into a retraction cavity disposed inside the trigger and the front tip of the needle is retained inside the body of the device.

BRIEF DESCRIPTION OF THE DRAWINGS

The apparatus of the invention is further described and explained in relation to the following drawings wherein:

FIG. 1 is a simplified perspective view of a preferred embodiment of a device useful for collecting a bodily fluid such as blood wherein the device is oriented in a substantially vertical position with the forwardly extending portion of the device pointed in a generally downward direction;

FIG. 2 is an exploded view of the device of FIG. 1;

FIG. 5 is a left end view of the device of FIG. 1 when oriented as in FIG. 4;

FIG. 6 is a cross-sectional elevation view taken along line 6-6 of the device of FIG. 3, with the device shown in its pre-use configuration prior to insertion of a fluid collection tube inside the device;

FIG. 7 is a cross-sectional elevation view of the device of FIG. 6 following insertion of a fluid collection tube inside the device;

FIG. 8 is a cross-sectional elevation view of the device of FIG. 6 in its post-use and post-retraction configuration, with the retraction spring expanded and with the front needle tip retracted inside the body of the device;

FIG. 9 is a simplified and reduced-size depiction of FIG. 4, with section lines showing the position and direction in which the cross-sectional view of FIG. 10 is taken;

FIG. 10 is a simplified cross-sectional elevation view taken along line 10-10 of FIG. 9;

FIG. 11 is an enlarged, detail view taken from the cross-sectional elevation view of FIG. 10, showing the lug ring, lug and the lug-contacting surface of the trigger in the pre-use, pre-retraction position;

FIG. 12 is the device as shown in FIG. 10, but with the trigger depressed relative to the body and with the lug ring and lug rotated to the retraction position;

FIG. 13 is an enlarged, detail view taken from the cross-sectional elevation view of FIG. 10, showing the lug ring, lug and the lug-contacting surface of the trigger in the retraction position;

FIG. 14 is the device as shown in FIG. 12, but following retraction; and

FIG. 15 is an enlarged detail view taken from FIG. 7.

Like reference numerals are used to describe like parts in all Figures of the Drawings.

DESCRIPTION OF A PREFERRED EMBODIMENT

Figure 3:
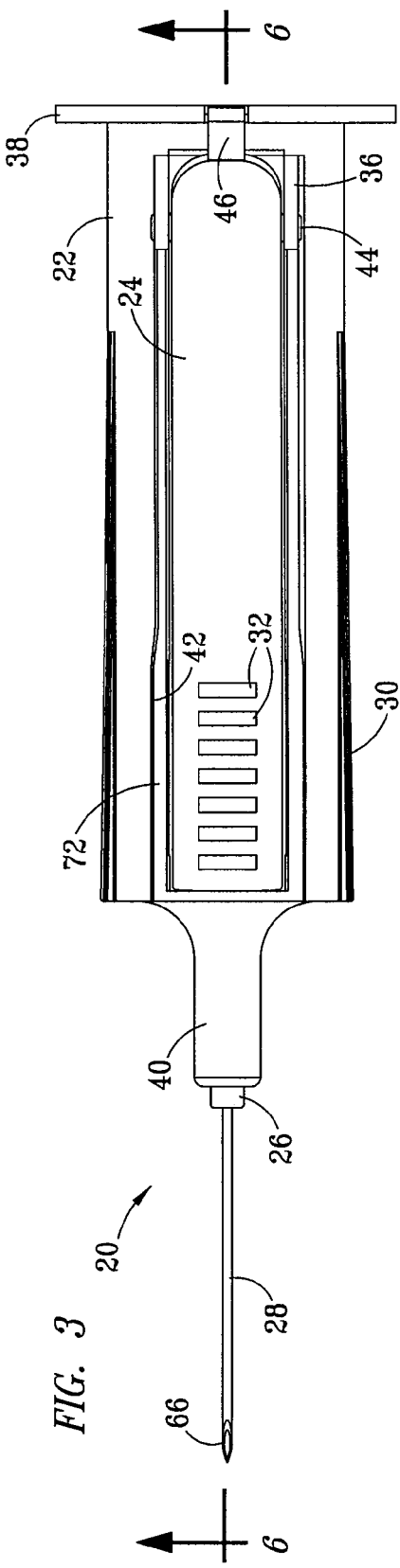
FIG. 3 is a top plan view of the device of FIG. 1 when oriented in a horizontal position.

Device 20, as depicted wholly or in part in the various figures of the drawings, is desirably configured to facilitate the collection of bodily fluids, and more preferably, vascular fluids, from the body of a patient. Device 20 is typically used in conjunction with a blood collection tube as depicted, for example, in FIGS. 7 and 8, and further discussed below in relation to those figures. Device 20 desirably includes a needle having two pointed ends connected by a common bore that places them in fluid communication so that any fluid flowing into the front end, for example, can flow out the back end unless somehow impeded from doing so. The needle is desirably supported inside device 20 by a needle holder. The rearwardly facing pointed end of the needle is desirably covered with a flexible rubber sheath that is secured by friction, adhesive, or the like, to the rear end of the needle holder.

During clinical procedures intended to draw samples of a bodily fluid such as vascular blood from a patient, the forwardly projecting end of the needle is inserted into a vein or artery of a patient. Device 20 is provided with textured gripping surfaces to facilitate this effort, and the underside of device 20 is desirably substantially flat to allow the needle to be inserted at a nearly-flat angle relative to the patient's body. A fluid collection tube having a rubber stopper is desirably inserted into device 20 through an opening at the rear, and is moved forwardly inside device 20 until the rear end of the needle meets the resistance of the rubber stopper. When this occurs, because the rubber sheath is typically much more flexible than the rubber stopper, the needle tip punctures the sheath and the sheath collapses around the needle and the needle tip advances through the stopper. Once the rearwardly facing needle tip penetrates the stopper of the fluid collection tube, the bodily fluid flowing into the needle from the patient at the front end can flow through the needle and into the fluid collection tube. Fluid collection tubes are typically evacuated sufficiently to enable the fluid to flow into the tube without venting. When the desired volume of fluid has been collected, the tube is withdrawn from device 20, and as the rearwardly facing needle tip exits the stopper, the rubber sheath again expands down and over the now-exposed needle tip. The rubber used to made the rubber sheath desirably has sufficient elasticity that that the hole made by the needle closes when the needle is withdrawn, thereby preventing unintended fluid flow out the back of the needle while the front needle tip is still inserted in the patient.

At this stage of a clinical vascular fluid draw using conventional devices, the front needle tip would be withdrawn from the vein or artery of a patient, and the bare needle tip, possibly contaminated with a blood-borne pathogen, would pose a risk to clinicians until disposed of in an approved sharps container or the like. In many cases, this is the time when accidental needle sticks and infections occur. For this reason, device 20 is specially adapted and configured to withdraw the front needle tip from the patient and into the body of device 20 to reduce substantially any opportunity for an accidental needle stick or contamination by direct contact with the needle tip or the bodily fluid carried on it.

Referring to FIGS. 1-2, device 20 desirably includes body 22, elongated trigger 24, needle holder 50 and retractable needle 28. Body 22 desirably further comprises a front opening at the forward end of nose 40, rear opening 34, outwardly projecting flange member 38, and finger grips 30 disposed on each side. Finger grips 32 are also desirably present on the upwardly facing end of trigger 24 that is opposite hinge supports 36 of body 22, to which trigger 24 is pivotably connected. Front tip 26 of needle holder 50, to which retractable needle 28 is attached, desirably extends slightly past nose 40 of body 22 through the front opening of nose 40 that is not visible in FIGS. 1-2.

Figure 4:
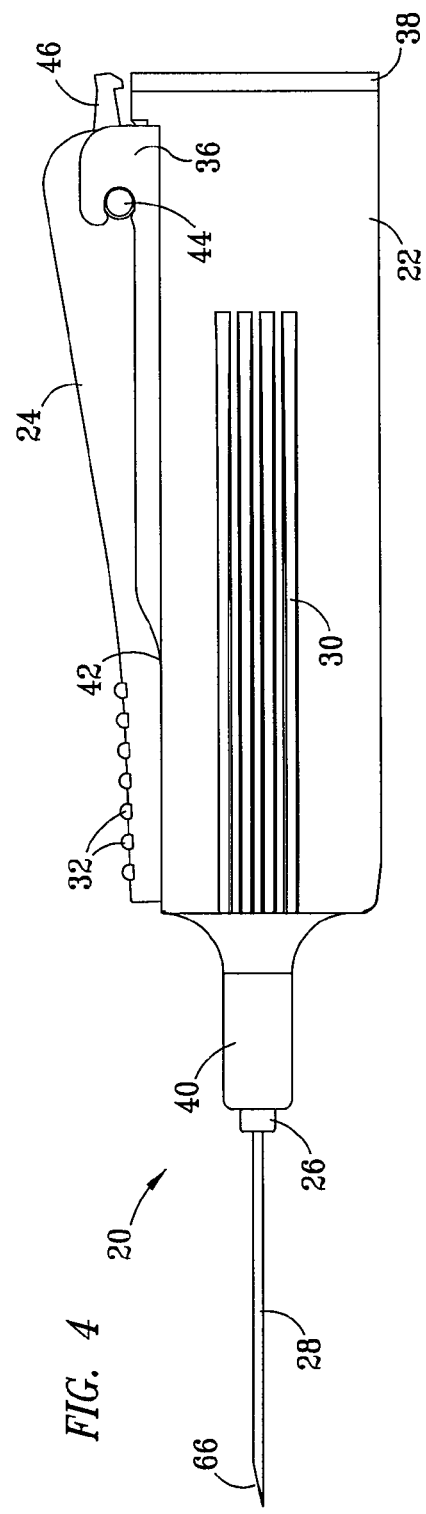
FIG. 4 is a side elevation view of the device of FIG. 1 when oriented as in FIG. 2.

The structure and assembly of device 20 are further described and explained in relation to FIGS. 1-7. Trigger 24 is preferably an elongated member, generally shaped like an inverted U, having a forwardly facing open end 96 (FIG. 7) and an oppositely disposed closed end that comprises two opposing, laterally projecting bosses 44 (FIGS. 2, 4 and 5). In this embodiment of the invention, bosses 44 serve as hinge pins that snap into engagement with hinge supports 36 on body 22 during assembly of device 20, although other similarly effective structures can likewise be used to pivotably connect the rear portion of trigger 24 to body 22. The frictional engagement between bosses 44 and hinge supports 36 is desirably sufficient to prevent trigger 24 from accidentally detaching from body 22 during use of device 20 but not so great as to provide significant resistance to the rotation of bosses 44 inside the cooperating recesses of hinge supports 36 after assembly. A rearwardly projecting stop member 46 is preferably provided to limit the upward rotation of trigger 24 relative to body 22 during use of device 20. The underside of trigger 24 (when oriented as in FIG. 7) is preferably open for a major portion of its length, with a bottom wall section 47 disposed near the rear. As is discussed in greater detail below, the interior space within trigger 24 serves as a retraction cavity 90 into which a major portion of retractable needle 28 and other portions of the needle retraction assembly are received during retraction following collection of the bodily fluid. A textured finger gripping surface comprising, for example, a plurality of spaced-apart laterally disposed ridges 32, is preferably provided on the top surface of trigger 24 adjacent free open end 96. Referring to FIG. 7, an undercut lug-contacting surface 94 facing generally downward relative to body 22 is also desirably provided adjacent open end 96. The function of lug-contacting surface 94 is further described below.

Body 22 has a generally tubular sidewall defining an interior cavity 92 that, in this preferred embodiment, has a diameter sufficient to receive a conventional fluid receptacle such as blood collection tube 76 that is slidably inserted through rear opening 34 during use of device, as shown in FIGS. 6 and 7. The sidewall of body 22 desirably serves as a guide to maintain blood collection tube 76 in substantially coaxial alignment with body 22 and needle 28 during use of device 20, and the length of body 22 is desirably such that a portion of tube 76 remains easily graspable by a clinician to facilitate removal of tube 76 following collection of a bodily fluid. Referring to FIGS. 1-5, finger grips 30 comprising, for example, surface sections textured with a plurality of closely spaced ridges are desirably provided on each side of body 22 to assist a clinician in gripping body 22 during use of device 20.

Referring particularly to FIGS. 2-4, 6 and 7, body 22 preferably further comprises an elongate, longitudinally extending, upwardly facing slot 72 that is sized and configured to receive a portion of trigger 24 into the slot as open end 96 of trigger 24 is pivoted downwardly relative to body 22 from hinge supports 36. A recessed forward portion 42 at the sides and front of slot 72 facilitates the downward movement of the front of trigger 24 into slot 72. The front end of body 22 desirably comprises a tapered nose 40 having an inwardly stepped inside diameter and a front opening with an inside diameter slightly larger than the outside diameter of front tip 26 of needle holder 50. Referring to FIGS. 1 and 7, the length of nose 40 is desirably such that front tip 26 of needle holder 50 extends slightly beyond the nose to facilitate attachment of needle 28 to needle holder 50 following the installation of needle holder 50 inside body 22 if desired.

Referring particularly to FIGS. 2 and 7, a needle retraction assembly that preferably comprises lug ring 62, needle holder 50 and compressible retraction spring 70 is desirably seated inside the front portion of body 22. Although it will be appreciated that other similarly effective structures can likewise be used to seat the needle retraction assembly inside the front portion of body 22, one satisfactory structure comprises a plurality of circumferentially spaced hooks or arcuate segments 104, 106 that are configured in such manner and flexible enough to permit passage of lug ring 62 in a forwardly direction during installation but are configured in such manner and are stiff enough to retain the needle retraction assembly in the axial position shown in FIG. 7 against the biasing force of compressed spring 70 prior to retraction. When seated and supported in this manner inside body 22, lug ring 62 is rotatable around the longitudinal axis of device 20 but such rotational movement is limited by other structure as described below in relation to FIGS. 10-14. Needle holder 50 preferably comprises a centrally disposed longitudinal bore that is sized and configured to allow the passage of needle 28 through the bore. A transverse flange 52 is desirably provided on the outside of needle holder 50. The transverse flange 52 is desirably sized and configured to retain compressed retraction spring 70 disposed around needle holder 50 in nose 40. The forward end of spring 70 desirably abuts an annular shoulder just rearwardly of the front opening of nose 40.

During assembly of device 20, a flexible elastomeric sheath 56 having an open end 58 and a closed end 74 is desirably attached, such as by frictional engagement, to head 54 and neck 60 of needle holder 50. Lug ring 62 is placed over sheath 56 and head 54 of needle holder 50. Front tip 26 of needle holder 50 is inserted into spring 70, and that assembly is inserted into body 22 with lug ring 62 positioned so that centrally disposed aperture 102 in lug ring 62 (visible, for example, in FIGS. 10 and 14) is not aligned to permit passage of transverse flange 52 (visible in FIG. 12) of needle holder 50 through aperture 102. When lug ring 62 is disposed in this way, needle holder 50 is preferably maintained in the position shown in FIGS. 6 and 7 prior to needle retraction. Lug ring 62 preferably further comprises at least one outwardly projecting lug 64, as seen for example in FIGS. 10-14 and discussed in greater detail below. Following seating of the needle retraction assembly inside body 22, rear needle tip 68 of needle 28 can be inserted into and through front tip 26 of needle holder 50 and advanced rearwardly until rear needle tip 68 is near but not touching closed end 74 (FIG. 2) of flexible elastomeric sheath 56. When properly positioned relative to needle holder 50, needle 28 is preferably attached to needle holder 50 using any suitable conventional means such as an adhesive, laser welding, or the like. As seen, for example, in FIGS. 2 and 7, needle 28 preferably has an upwardly facing bevel at front needle tip 66 and an oppositely facing bevel at rear needle tip 68.

Referring to FIGS. 1-5, body 22, trigger 24, lug ring 62 and needle holder 50 are all desirably made of an injection moldable polymeric resin of the type commonly used for manufacturing similar medical devices, but the use of polymeric materials is not required. Where polymeric materials are used, it is not required that all the parts be made using the same polymeric material.

Referring to FIG. 6, one preferred embodiment of device 20 as described herein is depicted in its pre-use configuration, although it will be appreciated that a needle cover (not shown) can also be provided to protect front needle tip 66 prior to use even though device 20 is desirably shipped and stored inside a sterile package. In the pre-use position, the front portion of trigger 24 can pivot downwardly into a resting position inside the upwardly facing slot 72 of body 22 as shown. As a fluid collection tube 76 is advanced forwardly into body 22 through rear opening 34 as indicated by arrow 84, the top of rubber stopper 80 contacts the underside of trigger 24 and causes the front end of trigger 24 to rotate upwardly relative to body 22 to the position shown in FIG. 7. When trigger 24 is in the position of FIG. 7, rearwardly facing projection 46 of trigger 24 contacts and abuts against the bottom of notch 48 (visible in FIG. 2) to limit the upward motion of trigger 24 relative to body 22. As fluid collection tube 76 (FIG. 6) advances, rear needle tip 68 penetrates elastomeric sheath 56 and then penetrates rubber stopper 80 to establish fluid communication with interior 92 of tube member 78. As this occurs (best seen in FIG. 15 taken from FIG. 7), elastomeric sheath 56 is crumpled into the annular space around needle 28 at the front of rubber stopper 80.

Referring to FIGS. 10 and 11, lug 64, which preferably projects radially outward from lug ring 62, is desirably positioned in a detent behind a smoothly configured boss 100 projecting inwardly from a portion of body 22 opposite lug 64. Boss 100 prevents lug ring 62 from rotating relative to body 22 and transverse flange 52 of needle holder 50 prior to needle retraction. When lug ring 62 is positioned as shown in FIGS. 10 and 11, transverse flange 52 of the needle holder cannot pass through aperture 102 in lug ring 62. Also, the biasing force of spring 70 (FIG. 7) applied against the forwardly facing surface of transverse flange 52 is constrained by lug ring 62 until lug ring 62 is rotatably repositioned inside body 22. It should be appreciated upon reading this disclosure that transverse flange 52 and aperture 102 can each have an infinite number of different shapes, provided however, that the relative size and shape of transverse flange 52 and aperture 102 are such that transverse flange 52 can pass through aperture 102 only when lug ring 62 has been rotated from the constrained position shown in FIGS. 10-11 to an unconstrained position as shown in FIGS. 12-14.

Referring to FIG. 8, after the fluid collection tube has been filled to the desired extent with the bodily fluid withdrawn from a patient, the clinician using device 20 will grasp and withdraw collection tube 76 from cavity 86 as indicated by arrow 87. As this happens, rubber stopper 80 seals off tube 76 to prevent fluid leakage from the tube and elastomeric sheath expands back over rear needle tip 68 to prevent leakage of any bodily fluid still contained in needle 28 out the back of body 22. Needle 28 can then be retracted directly from the patient by depressing the free end of trigger 24 inside the upwardly facing slot of body 22 past the resting point shown in FIG. 6 to a point where needle retraction occurs.

Referring to FIGS. 12-14, as the front end of trigger 24 is depressed inside body 22, downwardly facing contact surface 94 of trigger 24 contacts the opposed, upwardly facing surface of lug 64 of lug ring 62, thereby forcing lug 64 past projection 100 of body 22 and simultaneously rotating lug ring 62 as indicated by arrow 65 (FIG. 13) to a position where transverse flange 52 and aperture 102 are aligned in a position where transverse flange 52 is no longer constrained by lug ring 62. Referring again to FIG. 8, when lug ring 62 reaches the position where needle holder 50 is released, spring 70 expands rapidly and, acting on the front surface of transverse flange 52 of needle holder 50, drives needle holder 50 with elastomeric sheath 56 and needle 28 attached, rearwardly into retraction cavity 90 of trigger 24. When this occurs, lug ring 62 and lug 64 remain in the position shown in FIG. 12, needle 28 is inclined upwardly, and front end tip 66 of needle 28 is retracted inside nose 40 of body 22 to a position where no one, whether it be the patient, a clinician or another bystander, is thereafter subjected to the possibility of an accidental needle stick injury and/or infection from the potentially contaminated needle. Because needle 28 is then captured inside device 20, the possible reuse of device 20 is also eliminated.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

We claim:

1. A device useful for collecting bodily fluid from a patient, the device comprising:
    a body having a forwardly projecting, rearwardly biased, releasably constrained, selectively retractable needle, the body being configured to receive a fluid collection tube into selectively releasable fluid communication with a rear end of the retractable needle;
    an elongate trigger comprising a retraction cavity, a rear portion hinged to the body, an open front portion permitting access to the retraction cavity, and a lug-contacting surface selectively engageable with a lug ring rotatably mounted inside the body;
    whereby pivotable movement of the trigger relative to the body following release of the fluid collection tube from the body rotates the lug ring and thereby releases the rearwardly biased needle to retract into the retraction cavity.

2. The device of claim 1 wherein the bodily fluid is blood.

3. The device of claim 1 wherein the fluid collection tube is a blood collection tube.

4. The device of claim 1 wherein the retractable needle has sharp front and rear needle tips.

5. The device of claim 4 wherein the retractable needle has an upwardly facing bevel on the front needle tip and a downwardly facing bevel on the rear needle tip.

6. The device of claim 4 wherein the rear needle tip is surrounded by a flexible elastomeric sheath.

7. The device of claim 6 wherein the sheath is attached to a needle holder seated inside the body.

8. The device of claim 1 wherein the retractable needle is attached to a needle holder seated inside the body.

9. The device of claim 8 wherein the needle holder has a transverse flange.

10. The device of claim 8 wherein a portion of the needle holder projects forwardly of the body.

11. The device of claim 8 wherein the needle holder is constrained by the lug ring.

12. The device of claim 11 wherein the lug ring comprises a centrally disposed aperture alignable with a transverse flange of the needle holder.

13. The device of claim 1 wherein the needle is rearwardly biased by a compressed retraction spring.

14. The device of claim 1 wherein retractable needle is constrained by the lug ring.

15. The device of claim 1 wherein the body comprises an open back end into which a fluid collection tube can be releasably inserted.

16. The device of claim 1 wherein the body comprises an upwardly facing slot.

17. The device of claim 16 wherein the trigger is depressed inside the slot to rotate the lug ring.

18. The device of claim 1 wherein the body comprises at least one transversely projecting flange member.

19. The device of claim 18 wherein the at least one transversely projecting flange member has a substantially flat bottom.

20. The device of claim 1 wherein the activation member of the trigger is a surface engageable with a lug projecting from the lug ring.

21. The device of claim 1 wherein the body, trigger and lug ring are made of molded plastic.

\* \* \* \* \*